United States Patent [19]

Goddard

[11] B 4,001,272
[45] Jan. 4, 1977

[54] HERBICIDAL 2-FLUORO-4-HALO-PHENYL-4,5,6,7-TETRAHYDRO-2H-ISOINDOLE-1,3-DIONES

[75] Inventor: Steven Jerome Goddard, West Grove, Pa.

[73] Assignee: E. I. Du Pont de Nemours and Company, Wilmington, Del.

[22] Filed: Dec. 24, 1974

[21] Appl. No.: 536,322

[44] Published under the second Trial Voluntary Protest Program on March 23, 1976 as document No. B 536,322.

Related U.S. Application Data

[63] Continuation-in-part of Ser. No. 502,968, Sept. 3, 1974, abandoned.

[52] U.S. Cl. .............................. 260/326 HL; 71/96
[51] Int. Cl.$^2$ ........................................ C07D 209/48
[58] Field of Search ............................ 260/326 HL

[56] References Cited
FOREIGN PATENTS OR APPLICATIONS
2,119,703   7/1972   France .................. 260/326 HL

*Primary Examiner*—Lewis Gotts
*Assistant Examiner*—S. P. Williams

[57] ABSTRACT

This invention relates to herbicidal 2-fluoro-4-halophenyl-4,5,6,7-tetrahydro-2H-isoindole-1,3-diones. These compounds may be used for selective weed control in certain crops or for total vegetation control.

3 Claims, No Drawings

HERBICIDAL 2-FLUORO-4-HALO-PHENYL-4,5,6,7-TETRAHYDRO-2H-ISOINDOLE-1,3-DIONES

RELATED APPLICATION

This application is a continuation-in-part of my earlier filed application U.S. Ser. No. 502,968 filed Sept. 3, 1974, now abandoned, entitled 2-(4-CHLORO-2-FLUOROPHENYL)-4,5,6,7-TETRAHYDRO-2H-ISOINDOLE-1,3DIONE AND 2-(4-BROMO-2-FLUOROPHENYL)-4,5,6,7-TETRAHYDRO-2H-ISOINDOLE-1,3-DIONE AND THEIR USE AS HERBICIDES.

BACKGROUND OF THE INVENTION

A number of isoindole-type compounds are known in the prior art. Recently, in German Offenlegungsschrift No. 2,165,651 a group of isoindole-1,3-diones which are useful as herbicides was disclosed. The general formula for the isoindole-1,3-diones is as follows:

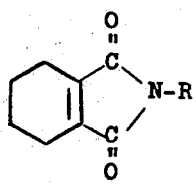

wherein R may be an aryl, aralkyl or benzyl optionally substituted with 1 to 5 halogen atoms; hydroxy, nitro, cyano, thiocyano, carboxy, halogenated alkyl, or alkyl, or alkoxy, lower alkylthio, phenyl groupings and a group having the configuration —O—CH$_2$A may also be substituted therein, wherein A is a phenyl or a naphthyl group, wherein the phenyl group may have one or more substitutions therein, such as halogen atoms, nitro groupings, lower alkyl groupings or lower alkoxy groupings.

Typical of the compounds disclosed in the Offenlegungsschrift is the compound of Example 1:

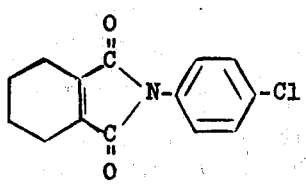

It should be emphasized that several thousand compounds are disclosed within the broad description of the Offenlegungsschrift.

The compounds of the present invention result from efforts to develop superior herbicidal compounds.

SUMMARY OF THE INVENTION

This invention relates to novel compounds of the following formula and their use as herbicides:

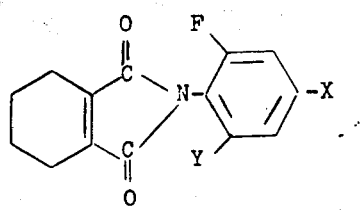  Formula I wherein X is Cl, Br or F, and Y is H or F, provided that when X is F, Y is F. It is preferred that X is Cl and Y is H.

This invention also includes herbicidal compositions containing the above compounds as active ingredients and methods of controlling undesirable vegetation by applying the compounds and/or compositions to the locus of such undesired vegetation.

DESCRIPTION OF THE INVENTION

Preferred compounds

The preferred compound of the instant invention is 2-(4-chloro-2-fluorophenyl)-4,5,6,7-tetrahydro-2H-isoindole-1,3-dione.

Synthesis of the compounds

The compounds of Formula I can be made by the processes described and exemplified below.

The preparation of the subject compounds begins with 2-fluoroaniline and 2'-fluoro-acetanilide, which can be prepared as described by G. Schiemann and H. G. Baumgarten, Chem. Berichte, 70; 1416 (1937). The process to be utilized in order to form the compounds of the instant invention is as follows:

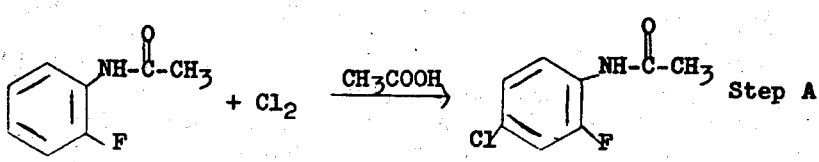 Step A

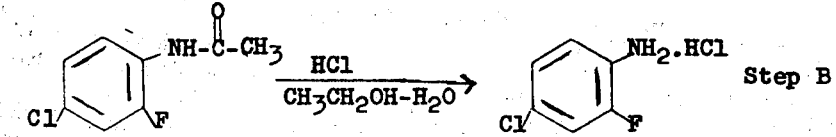 Step B

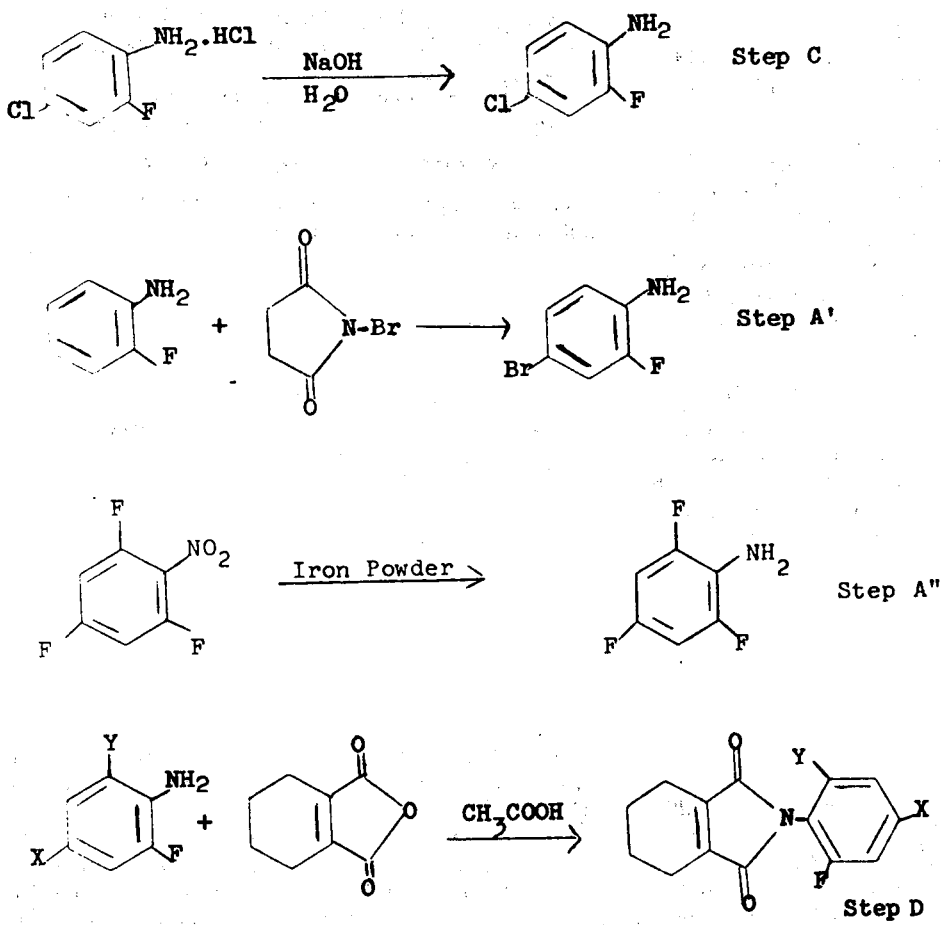

wherein X is Cl, Br or F, and Y is H or F, provided that when X is F, Y is F. It is preferred that X is Cl and Y is H.

Step A

The reaction of 2'-fluoroacetanilide and chlorine in acetic acid is well known to those skilled in the art, e.g., W. W. Reed and K. J. P. Orton, J. Chem. Soc., 91, 1543 (1907) for the chlorination of acetanilide to obtain 2',4'-dichloroacetanilide. The reaction takes place at 25°–30°C over several hours at atmospheric pressure.

Step B

The chlorofluoroacetanilide is refluxed in a mixture of a lower alcohol (50%) and concentrated hydrochloric acid (50%) for several hours at 70°–90°C and atmospheric pressure. The solvent mixture is removed at a reduced pressure of 100 to 300 mm.Hg and 20°–50°C to leave a residue of the hydrochloride salt of 4-chloro-2-fluoroaniline.

Step C

By treatment of an aqueous solution of the hydrochloride salt of 4-chloro-2fluoroaniline with an alkali metal hydroxide solution, the free 4-chloro-2-fluoroaniline is extracted into a suitable water-immiscible organic solvent such as ethyl ether or methylene chloride. The crude 4-chloro-2-fluoroaniline is isolated by removal of the organic solvent under reduced pressure of 100 to 300 mm.Hg. at 20°–50°C.

Step A'

The reaction of 2-fluoroaniline and N-bromosuccinimide in an inert organic solvent such as methylene chloride is well known to those skilled in the art, e.g., J. B. Wommack et al., J. Het. Chem., 6, 243 (1969). The exothermic reaction takes place at 0°C over several hours. The resulting reaction mixture is washed with water several times and dried with an appropriate drying agent such as anhydrous sodium sulfate. The 4-bromo-2-fluoroaniline is recovered by removal of the organic solvent under reduced pressure of 100 to 300 mm.Hg. at 20°–50°C.

Step A"

The synthesis of 2,4,6-trifluoroaniline from 1,3,5-trifluoro-2-nitrobenzene uses the same procedure as that described by G. Schiemann and M. Seyhan [chem. Ber., 70, 2396 (1937)] for the preparation of 2,4-difluoroaniline. The preparation of 1,3,5-trifluoro-2-nitrobenzene is described by V. I. Siele and H. J. Matsuguma, U.S. Dept. Com., Office Serv., P B Rept. 145, 510, p. 1 (1960) [Chem. Abst. 56, 15394C (1962)].

Step D

The reaction of each of the di- or trihalo anilines (from Step C, A' or A") and 3,4,5,6-tetrahyrophthalic anhydride in acetic acid to form the corresponding imide is demonstrated in Netherlands Pat. No. 7,117,690 (Mitsubishi Chem. Ind.). The dihaloaniline and 3,4,5,6-tetrahydrophthalic anhydride are refluxed in glacial acetic acid at temperatures of 115°–120°C and atmospheric pressure for several hours. The di- or trihalophenyl-4,5,6,7-tetrahydro-2H-isoindole-1,3-dione is isolated by precipitation with water followed by filtration.

The compounds which may be prepared by the instant process are as follows:

2-(4-chloro-2-fluorophenyl)-4,5,6,7-tetrahydro-2H-isoindole-1,3-dione m.p. 76.5°–78.0°C
2-(4-bromo-2-fluorophenyl)-4,5,6,7-tetrahydro-2H-isoindole-1,3-dione m.p. 102.0°–102.5°C
2-(2,4-difluorphenyl)-4,5,6,7-tetrahydro-2H-isoindole-1,3-dione m.p. 73°–74°C
2-(2,4,6-trifluorophenyl)-4,5,6,7-tetrahydro-2H-isoindole-1,3-dione m.p. 91°–92°C The following examples further illustrate this method for synthesis of compounds of this invention. All parts are by weight and all temperatures in degrees centigrade unless otherwise indicated.

EXAMPLE 1

Preparation of
2-(4-chloro-2-fluorophenyl)-4,5,6,7-tetrahydro2H-isoindole-1,3-dione A solution of 140 parts of 2'-fluoroacetanilide in 500 parts glacial acetic acid was treated with 71 parts of chlorine during one hour at 25°–27°C with ice-water cooling. While stirring for 4 hours at 25°–27°C, 4'-chloro-2'-fluoroacetanilide precipitated. After collecting the product by filtration, the filtrate was poured over 2000 parts of ice. The resulting second portion of product precipitated was collected by filtration, combined with the first portion and recrystallized from 700 parts of methanol at −45°C. to yield 119 parts of 4'-chloro-2'-fluoroacetanilide as white crystals melting at 152°–155°C.

A mixture of 119 parts of 4'-chloro-2'-fluoroacetanilide in 475 parts of ethanol and 200 parts of 37% hydrochloric acid was refluxed for 17 hours and the solvent removed under a reduced pressure of 300 mm.Hg. to yield the moist, solid hydrochloride salt of 4-chloro-2-fluoroaniline.

The moist, solid hydrochloride salt of 4-chloro-2-fluoroaniline was cooled in an ice-acetone bath and treated at 10°C with 50% aqueous sodium hydroxide until pH 11 is reached. The resulting two-phase mixture was extracted four times; 500 parts of methylene chloride were used for each extraction. The combined organic extracts were dried with anhydrous sodium sulfate and the solvent removed under reduced pressure of 300 mm.Hg. to leave 89 parts of light brown, oily 4-chloro-2-fluoroaniline, $N_D^{25} = 1.5541$.

A solution of 88 parts of 3,4,5,6-tetrahydrophthalic anhydride in 2000 parts of glacial acetic acid was treated with 84 parts of 4-chloro-2-fluoroaniline at once and stirred for one hour. After refluxing for 19 hours, 1000 parts of acetic acid were distilled from the reaction mixture. The residue from the distillation was poured over 3000 parts of ice. The resulting crystals were filtered and recrystallized from 700 parts of methanol at −40°C after activated carbon treatment, to yield 117 parts off-white crystals of 2-(4-chloro-2-fluorophenyl)-4,5,6,7-tetrahydro-2H-isoindole-1,3-dione melting at 76.5°–78.0°C.

EXAMPLE 2

Preparation of
2-(4-bromo-2-fluorophenyl)-4,5,6,7-tetrahydro-2H-isoindole-1,3-dione A solution of 100 parts of 2-fluoroaniline in 400 parts of methylene chloride was cooled to 0°C and treated batchwise with 160 parts of solid N-bromosuccinimide over 2 hours at 0°C. After stirring for 20 minutes, the dark red mixture was washed four times; 200 parts of cold water were used for each washing. The red organic phase was dried with anhydrous sodium sulfate and evaporated under 300 mm.Hg. to 164 parts of brown, oily 4-bromo-2-fluoroaniline, $N_D^{25}$ : 1.5885.

A solution of 10 parts of 3,4,5,6-tetrahydrophthalic anhydride in 100 parts of glacial acetic acid was treated in one portion with 11 parts of 4-bromo-2-fluoroaniline and was stirred for 30 minutes. The reaction mixture was refluxed for 16 hours and then poured over 200 parts ice. The resulting purple crystals were filtered and recrystallized from 100 parts methanol at −40°C to yield 13 parts of pink plates of 2-(4-bromo-2-fluorophenyl)-4,5,6,7-tetrahydro-2H-isoindole-1,3-dione melting at 102.0°–102.5°C.

EXAMPLE 3

A solution of 5 parts of 3,4,5,6-tetrahydrophthalic anhydride in 100 parts of glacial acetic acid was treated with 4.3 parts of 2,4-difluoroaniline at once and stirred for one hour. After refluxing for 20 hours, the reaction mixture was poured over 200 parts of ice. The resulting crystals were filtered and recrystallized from 70 parts of methanol at −40°C to yield 5 parts off-white crystals of 2-(2,4-difluorophenyl)-4,5,6,7-tetrahydro-2H-isoindole-1,3-dione melting at 73°–74°C.

EXAMPLE 4

A solution of 5.3 parts of 3,4,5,6-tetrahydrophthalic anhydride in 100 parts of glacial acetic acid was treated with 5 parts of 2,4,6-trifluoroaniline at once. After refluxing for 24 hours, the acetic acid was stripped from the reaction mixture under 300 mm hg pressure. The residue was dissolved in 100 parts of methylene chloride and washed with 100 parts of 10% aqueous sodium carbonate. After drying over anhydrous sodium sulfate, the solution was stripped under 300 mm hg pressure. The resulting pink oil was crystallized from 70 parts of methanol at −40°C to yield 4.7 parts white crystals of 2-(2,4,6-trifluorophenyl)-4,5,6,7-tetrahydro-2H-isoindole-1,3-dione melting at 91°–92°C.

FORMULATIONS OF THE COMPOUNDS

The formulations of the compounds of Formula I for use in this invention can be prepared in conventional ways. They include dusts, granules, pellets, solutions, suspensions, emulsions, wettable powders, emulsifiable concentrates, and the like. Many of these can be applied directly. Sprayable formulations can be extended in suitable media and used at spray volumes of from a few pints to several hundred gallons per acre. High strength compositions are primarily used as intermediates for further formulation. The formulations, broadly, contain about 1% to 99% by weight of active ingredient(s) and at least one of (a) about 0.1% to 20% surfactant(s) and (b) about 5% to 99% solid or liquid diluent(s). More specifically, they will contain these ingredients in the following approximate proportions.

| | Active % Ingredient | % Diluent | % Surfactant |
|---|---|---|---|
| Wettable Powders | 20–90 | 0–74 | 1–10 |
| Oil Suspensions Emulsions, Solutions (Including Emulsifiable Concentrates) | 5–50 | 40–95 | 0–10 |
| Aqueous Suspensions | 10–50 | 40–89 | 1–10 |
| Dusts | 1–25 | 70–99 | 0–5 |
| Granules and Pellets | 1–35 | 65–99 | 0–15 |

| | Active % Ingredient | % Diluent | % Surfactant |
|---|---|---|---|
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable and are achieved by incorporation into the formulation or by tank mixing.

The compounds of Formula I can be combined with other herbicides and are particularly useful in combination with bromacil [3-(sec-butyl)-5-bromo-6-methyluracil], diuron-[3-(3,4-dichlorophenyl)-1,1-dimethylurea], paraquat[1,1'-dimethyl-4,4'-bipyridinum ion], m-(3,3-dimethylureido)-phenyl tert-butylcarbamate, 4-amino-6-tert-butyl-3-methylthio-as-triazin-5(4H)-one, and the s-triazines such as 2-chloro-4-ethylamino-6-isopropylamino-s-triazine, for controlling a broad spectrum of weeds.

Typical solid diluents are described in Watkins et al. "Handbook of Insecticide Dust Diluents and Carrier", 2nd Edition, Dorland Books, Caldwell, New Jersey. The more absorptive diluents are preferred for wettable powders and the denser ones for dusts. Typical liquid diluents and solvents are described in Marsden "Solvents Guide", 2nd Edition, Interscience, New York, 1950. Solubility under 0.1% is preferred for suspension concentrates; solution concentrates are preferably stable against phase separation at 0°C. "McCutcheon's Detergents and Emulsifiers Annual" Allured Publishing Corporation, Ridgewood, New Jersey, as well as Sisely and Wood "Encyclopedia of Surface-Active Agents", Chemical Publishing Co., New York, 1964, lists surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and usually grinding as in a hammer or fluid energy mill. Suspensions are prepared by wet milling (see, for example, Littler U.S. Pat. No. 3,060,084). Granules and pellets can be made by spraying the active material upon preformed granule carriers or by agglomeration techniques (see J. E. Browning "Agglomeration", *Chemical Engineering*, Dec. 4, 1967, pages 147 ff. and "Perry's Chemical Engineer's Handbook", 4th Edition, McGraw-Hill, New York, 1963, pages 8–59 ff.

For further information regarding the art of formulation see, for example:

H. M. Loux, U.S. Pat. No. 3,235,381, Feb. 15, 1966 Column 6, line 16 through column 7, line 19, and examples 10–41.

R. W. Luckenbaugh, U.S. Pat. No. 3,309,192, Mar. 14, 1967, Column 5, line 43 through column 7, line 62, and examples 8, 12, 15, 39, 41, 52, 53, 58, 132, 138–140, 162–164, 166, 167, and 169–182.

H. Gysin and E. Knusli, U.S. Pat. No. 2,891,855, June 23, 1959, Column 3, line 66 through column 5, line 17 and examples 1 through 4.

G. C. Klingman, "Weed Control as a Science", John Wiley & Sons, Inc., New York, 1961, pages 81 through 96.

J. D. Fryer and S. A. Evans, "Weed Control Handbook", 5th Edition, Blackwell Scientific Publications, Oxford, 1968, pages 101–103.

The following examples illustrate formulations of this invention. All parts are by weight unless otherwise indicated.

EXAMPLE 5

| Wettable Powder | |
|---|---|
| 2-(4-chloro-2-fluorophenyl)-4,5,6,7-tetrahydro-2H-isoindole-1,3-dione | 50% |
| Kaolinite | 38% |
| Diatomite | 5% |
| Synthetic silica | 3% |
| Sodium ligninsulfonate | 2% |
| Sodium alkylnaphthalenesulfonate | 2% |

The ingredients are blended, hammermilled to a fine powder, substantially all of which will pass through a 50-mesh sieve, and reblended.

EXAMPLE 6

| Wettable Powder | |
|---|---|
| 2-(4-bromo-2-fluorophenyl)-4,5,6,7-tetrahydro-2H-isoindole-1,3-dione | 50% |
| Kaolinite | 46% |
| Sodium alkylnaphthalenesulfonate | 2% |
| Low viscosity methyl cellulose | 2% |

The ingredients are blended, hammermilled to a fine powder, substantially all of which will pass through a 50-mesh sieve, and then reblended.

EXAMPLE 7

| Wettable Powder | |
|---|---|
| 2-(2,4-difluorophenyl)-4,5,6,7-tetrahydro-2H-isoindole-1,3-dione | 50% |
| Kaolinite | 46% |
| Sodium alkylnaphthalenesulfonate | 2% |
| Low viscosity methyl cellulose | 2% |

The ingredients are blended, hammermilled to a fine powder, substantially all of which will pass through a 50-mesh sieve, and then reblended.

EXAMPLE 8

| Wettable Powder | |
|---|---|
| 2-(2,4,6-trifluorophenyl)-4,5,6,7-tetrahydro-2H-isoindole-1,3-dione | 50% |
| Kaolinite | 46% |
| Sodium alkylnaphthalenesulfonate | 2% |
| Low viscosity methyl cellulose | 2% |

The ingredients are blended, hammermilled to a fine powder, substantially all of which will pass through a 50-mesh sieve, and then reblended.

UTILITY

The compounds of formula I are useful for the selective preemergence weed control of undesired vegetation such as rice, soybeans, peanuts, lima beans, green beans and squash. These compounds also have utility for the postemergence control of weeds in certain crops, for example, carrots. Furthermore, compounds of this invention can be used as directed treatments for the pre/post-emergence control of weeds in various crops including soybeans, peanuts, garden beans and row-planted rice. In addition, these compounds are useful wherever general weed control is required, such as industrial sites, railroad and utility rights-of-way, along fences, building foundations, parking and storage lots, etc.

The precise amount of the compounds of formula I to be used in any given situation will vary according to the particular end result desired, the use involved, the plant and soil involved, the formulation used, the mode of application, prevailing weather conditions, foliage density and like factors. Since so many variables play a role, it is not possible to state a rate of application suitable for all situations. Broadly speaking, the compounds of the invention are used at levels of about 0.125 to about 20 kilograms, preferably about 0.25 to about 10, per hectare. The lower rates in this range will generally be selected on lighter soils, soils low in organic matter content, for selective weed control in crops, or in situations where maximum persistence is not necessary.

Herbicial activity of compounds of this invention was discovered in a number of field tests.

In test A, soybeans, peanuts, lima beans, green beans

Test B involved a field sown to carrots and in which the following weed species emerged naturally: crabgrass (Digitaria sanquinalis), foxtails (Setaria spp.), barnyardgrass (Echinochloa crusgalli), pigweed (Amaranthus spp.), ragweed (Ambrosia artemisiifolia), velvetleaf (Abutilon theophrasti), smartweed (Polygonum spp.) and lambsquarters (Chenopodium album). Sixteen days after sowing, when all species of weeds had emerged, the plants were sprayed overall with a 50% wettable powder formulation of 2-(4-chloro-2-fluorophenyl)4,5,6,7-tetrahydro-2H-isoindole-1,3dione (Treatment I) in the form of an aqueous suspension, at rates of 0.5, 1.0, 2.0 and 4.0 kg/ha, and with 2-(4-chlorophenyl)-4,5,6,7-tetrahydro-2H-isoindole-1,3-dione (Treatment II) in the same form and at the same rates. The spray volume was 425 l/ha. The surfactant Tween 20* was added to all treatments in a concentration of 0.1% by weight. Six weeks after treatment, visual observations were made of percent weed control obtained and, for carrots, crop response. Pertinent data are presented in the following Table II.

*Tween 20 — A trademark of ICI of America which is the reaction product of sorbitan monolaurate with an average of 20 moles of ethylene oxide.

TABLE II

| TREATMENT I | | | TEST B % Control Naturally Emerging Weeds | | | | | | Crop Response |
|---|---|---|---|---|---|---|---|---|---|
| Rate kg/ha | Crabgrass | Foxtails | Barnyardgrass | Pigweed | Ragweed | Velvetleaf | Smartweed | Lambsquarters | Carrots |
| 0.5 | 60 | 70 | 65 | 92 | 98 | 100 | 99+ | 100 | 2 |
| 1.0 | 85 | 90 | 90 | 99 | 99+ | 100 | 100 | 100 | 3 |
| 2.0 | 90 | 94 | 94 | 100 | 100 | 100 | 100 | 100 | 5 |
| 4.0 | 100 | 99+ | 99+ | 100 | 100 | 100 | 100 | 100 | 6 |
| TREATMENT II | | | | | | | | | |
| Rate kg/ha | | | | | | | | | |
| 0.5 | 0 | 0 | 0 | 50 | 50 | 70 | 70 | 70 | 4 |
| 1.0 | 20 | 20 | 20 | 70 | 70 | 80 | 80 | 80 | 4 |
| 2.0 | 40 | 40 | 40 | 90 | 90 | 100 | 80 | 99 | 4 |
| 4.0 | 60 | 40 | 50 | 99 | 99+ | 100 | 99 | 99 | 4 | and squash were planted in a field infested with the following weed seeds: crabgrass (Digitaria sanquinalis), foxtails (Setaria spp.), barnyardgrass (Echinochloa crusgalli), pigweed (Amaranthus spp.), ragweed (Ambrosia artemisiifolia), velvetleaf (Abutilon theophrasti), purslane (Portulaca oleracea) and flower-of-an-hour (Hibiscus trionum). A 50% wettable powder formulation of 2-(4-chloro-2-fluorophenyl)-4,5,6,7-tetrahydro-2H-isoindole-1,3-dione was applied in the form of an aqueous suspension at rates of 0.125, 0.25, 0.5 and 1.0 kg/ha, each treatment replicated twice. The plots were rated for percent weed control and crop response seven weeks after treatment. Crop response was expressed on a scale of 0 = no injury to 10 = complete kill. The results obtained are shown in the following table.

The superiority of Treatment I was quite pronounced with respect to the naturally emerging weeds. In every one of the eight tests Treatment I produced % control results which were clearly superior to Treatment II. In particular, the control of crabgrass, foxtails and barnyardgrass with Treatment I was outstanding when compared to Treatment II.

Test C concerned preemergence weed control in rice. The field selected contained seeds of the following weed species: crabgrass (Digitaria sanquinalis), foxtail (Setaria spp.), barnyardgrass (Echinochloa crusgalli), pigweed (Amaranthus spp.), ragweed (Ambrosia artemisiifolia), velvetleaf (Abutilon theophrasti), purslane (Portulaca oleracea) and flower-of-an-hour (Hibiscus trionum). Two varieties of rice, CSM-3 and Nato, were planted at depths of both 1 and 2 cm. In addition, rice seedlings of both varieties were transplanted into the

TABLE I

| | | | | TEST A % Control | | | | | Crop Response | | | | |
|---|---|---|---|---|---|---|---|---|---|---|---|---|---|
| Rate kg/ha | Crabgrass | Foxtail | Barnyardgrass | Pigweed | Ragweed | Velvetleaf | Purslane | Flower-of-an-Hour | Squash | Green beans | Lima beans | Peanuts | Soybeans |
| 0.125 | 60 | 40 | 45 | 90 | 90 | 90 | 82 | 87 | 2 | 2 | 0 | 0 | 0 |
| 0.25 | 94 | 82 | 82 | 98 | 99 | 99 | 97 | 99 | 2 | 2.5 | 1 | 0 | 1.5 |
| 0.50 | 99 | 95 | 98 | 95 | 99 | 100 | 100 | 99 | 6 | 8 | 4 | 2 | 3 |
| 1.00 | 99 | 99 | 99 | 100 | 100 | 100 | 100 | 100 | 9.5 | 8.5 | 8.5 | 3.5 | 7.5 | field to be treated. Immediately thereafter, the plot was treated with an aqueous suspension of 2-(4-chloro-2-fluorophenyl)-4,5,6,7-tetrahydro-2H-isoindole-1,3-dione (Treatment I) at rates of 0.125 and 0.25 kg/ha, and an aqueous suspension of 2-(4-chlorophenyl)-4,5,6,7-tetrahydro-2H-isoindole-1,3dione (Treatment II) at rates of 0.25, 0.50, 1.00 and 2.00 kg/ha. The test chemicals had been formulated as 50% wettable powders. Overall spray volume was 540 l/ha. Ratings of percent weed control obtained and crop response were made 29 days after treatment, as described for test A. The ratings are summarized in the following Table III.

TABLE III

TEST C

| TREATMENT I Rate kg/ha | % Control | | | | | | | | Crop Response Rice | | | | | |
|---|---|---|---|---|---|---|---|---|---|---|---|---|---|---|
| | Crab-grass | Fox-tail | Barnyard-grass | Pig-weed | Rag-weed | Velvet-leaf | Purslane | Flower-of-an-Hour | CSM-3 | | | Nato | | |
| | | | | | | | | | 1 cm* | 2 cm* | T* | 1 cm* | 2 cm* | T* |
| 0.125 | 96 | 96 | 90 | 99 | 100 | 100 | 100 | 100 | 3 | 0 | 0 | 3 | 1 | 0 |
| 0.25 | 100 | 100 | 99 | 100 | 100 | 100 | 100 | 100 | 5 | 1 | 0 | 6 | 2 | 0 |
| TREATMENT II Rate kg/ha | | | | | | | | | | | | | | |
| 0.25 | 99 | 99 | 58 | 100 | 100 | 100 | 100 | 98 | 4 | 1 | 0 | 5 | 0 | 1 |
| 0.50 | 100 | 100 | 97 | 100 | 100 | 100 | 100 | 100 | 5 | 2 | 0 | 8 | 1 | 1 |
| 1.0 | 100 | 100 | 99 | 100 | 100 | 100 | 100 | 100 | 7 | 4 | 0 | 9 | 4 | 1 |
| 2.0 | 100 | 100 | 100 | 100 | 100 | 100 | 100 | 100 | 10 | 7 | 1 | 9 | 6 | 2 |

*1 cm and 2 cm = pl. depth;
T = transplanted.

What is claimed is:
1. The compound 2-(4-chloro-2-fluorophenyl)-4,5,6,7-tetrahydro-2H-isoindole-1,3-dione.
2. The compound 2-(4-bromo-2-fluorophenyl)-4,5,6,7-tetrahydro-2H-isoindole-1,3-dione.
3. The compound 2-(2,4-difluorophenyl)-4,5,6,7-tetrahydro-2H-isoindole-1,3-dione.

* * * * *